United States Patent [19]

Kitamura

[11] Patent Number: 5,667,777
[45] Date of Patent: Sep. 16, 1997

[54] DELIVERY OF GENE PRODUCTS VIA MESANGIAL CELLS

[75] Inventor: Masanori Kitamura, London, United Kingdom

[73] Assignee: The Jikei University School of Medicine, Tokyo, Japan

[21] Appl. No.: 480,301

[22] Filed: Jun. 7, 1995

Related U.S. Application Data

[62] Division of Ser. No. 153,769, Nov. 17, 1993, Pat. No. 5,580,558.

[51] Int. Cl.⁶ .................. A61K 48/00; A61K 31/12; C12N 5/06; C12N 15/63
[52] U.S. Cl. ............... 424/93.1; 424/93.2; 424/93.21; 435/69.1; 435/69.7; 435/71.1; 435/172.3; 935/62; 935/70; 935/71
[58] Field of Search .............. 424/93.21, 93.1, 424/93.2; 435/69.1, 69.7, 71.1, 172.3, 240.2, 240.21; 935/62, 70, 71, 34

[56] References Cited

U.S. PATENT DOCUMENTS 5,580,558  12/1996  Kitamura .................. 424/93.21

OTHER PUBLICATIONS

Woolf et al., *Kidney Int.*, 43 (Suppl. 39): S116–119, 1993.
Remuzzi et al., *Am. J. Physiol.*, 263, F562, 1992.
Brenner and Rector (eds.), *The Kidney*, 1, pp. 10–11, 1991.
Kawachi et al., *Clin. Exp. Immunol.*, 90, pp. 129–134, 1992.
Price et al., *Proc. Natl. Acad. Sci. USA*, 84, pp. 156–160, 1987.
Kitamura et al., *Kidney Int.*, 40, pp. 653–661, 1991.
Kashgarian and R.B. Sterzel, *Kidney Int.*, 41, pp. 524–529, 1992.
Baricos and Shah, *Kidney Int.*, 40, pp. 161–173, 1991.
Kawachi et al., *Clin. Exp. Immunol.*, 88, pp. 399–404, 1992.
Grossman et al., *Nature Genetics*, 6, 335–341, 1994.
Cline, *Pharmac. Ther.*, 29, 69–86, 1985.
Chowdhury et al., *Science*, 254, 1802–1805, 1991.
Tomita et al., *Nippon Rinsho.*, 50(12), 2878 Abstract Only, 1992.
Schlondorf, *FASEB J.*, 272–281, 1987.
*Culture of Animal Cells: A Manual of Basic Technology*, R. Ian Freshney, Ed., 197–214, 1987.

*Primary Examiner*—Brian R. Stanton
*Attorney, Agent, or Firm*—Thomas S. Borecki; Charles R. Mattenson; Mark S. Ellinger

[57] ABSTRACT

Disclosed are methods that achieve i) site-directed delivery, ii) in situ amplification, and iii) sustained expression of an exogenous gene product within renal glomeruli. An exogenous gene, *E. coli* β-galactosidase, was introduced into cultured rat mesangial cells using a replication-defective retrovirus, and stable infectants were administered to a rat kidney via the renal artery. In the injected kidney, the engineered, cultured mesangial cells populated 40% of glomeruli site-specifically. The gene product was detected throughout a 14-week period of observation. In an alternative method, engineered, cultured mesangial cells were injected into a kidney subjected to an antibody that induces mesangiolysis followed by mesangial regeneration. Under these conditions, expression of β-galactosidase was dramatically amplified in situ, and high level expression continued for at least 8 weeks.

6 Claims, No Drawings

DELIVERY OF GENE PRODUCTS VIA MESANGIAL CELLS

This is a divisional of U.S. application Ser. No. 08/153,761, filed Nov. 17, 1993, now U.S. Pat. No. 5,580,558.

FIELD OF THE INVENTION

This invention relates to delivery of cultured mesangial cells to a kidney of a mammal. More particularly, the invention relates to methods of administering cultured mesangial cells via a renal artery, from whence the cells are transported to and accumulate specifically in glomeruli of the kidney. The invention further relates to methods of expressing an exogenous gene product from such administered mesangial cells.

BACKGROUND OF THE INVENTION

Glomerular disease is one of the major causes of chronic renal failure. During the past five years, it has been suggested that various molecules such as cytokines/growth factors and proteolytic enzymes may be involved in the pathogenesis of glomerular injury as well as in the induction of proteinuria. M. Kashgarian and R. B. Sterzel, Kidney Int. 41, 524 (1992); W. H. Baricos and S. V. Shah, Kidney Int. 40, 161 (1991). However, many recent studies have used cultured cells or affected tissue, and therefore do not generate an understanding of the pathological role of such molecules in the generation of injury in vivo. An important challenge in this field is to identify molecular mediators pivotal in different types of glomerular damage, for example, through use of an appropriate in vivo system to select candidate molecules. Currently, there are no such methods appropriate for this purpose. Thus, it would be useful to establish methods suitable for assessing the pathophysiological function of specific molecules in situ, i.e., within renal glomeruli, using gene transfer technology.

The most commonly used techniques for delivering exogenous nucleic acid into cells involve the use of viral vectors. These vectors are advantageous in that they can infect large percentages of recipient cells and can integrate into the cell genome. The viral vectors are often constructed to be replication-defective once they have transfected a cell line. Other viral vectors that have been proposed or used for delivering nucleic acid into cells include adenovirus, adeno-associated virus, herpes virus and poliovirus vectors. The retroviral and adeno-associated virus vectors are most often proposed or used for ex vivo gene therapy, i.e., delivery of an exogenous DNA construct into cells temporarily removed from the body of the patient.

Hereinafter, exogenous nucleic acid construct or exogenous gene construct refers to a nucleic acid sequence originating outside a recipient cell and introduced into a recipient cell by a nucleic acid delivery technique. A nucleic acid or gene construct may be manufactured using recombinant DNA technology known in the art, or may be a nucleic acid fragment purified from a source material without further manipulation. The exogenous gene may be entirely composed of homologous sequences, i.e., sequences cloned, isolated, or derived from the same species from which the recipient cells derive. Alternatively, all or a portion of the exogenous gene may be composed of sequences from species other than the species from which the recipient cells derive, hereinafter termed heterologous sequences. The exogenous gene construct may be natural in that none of the regulatory sequences and coding sequences that may be a part of the gene are substantially or intentionally altered, or the exogenous gene construct may be chimeric in that sequence fragments from various sources are present in the final gene construct. Examples of exogenous nucleic acid constructs introduced into cells include constructs expressing bacterial proteins, oncogenes, cell surface molecules, and antisense sequences. Minoru, S., et al., EMBO J. 9:2835 (1990); Gossett, L., J. Cell Biol. 106:2127 (1988); Townsend, S. and Alison, P., Science 259:368 (1993); Trojan, J., et al., Science 259:94 (1993).

Gene transfer has been effected into various organs including bone marrow, skin, brain, heart, muscle, lung, liver, kidney, and arterial wall. J. W. Larrick and K. L. Burck, Gene Therapy: Application of Molecular Biology (Elsevier, New York 1991) chap. 5–7; H. Lin, et al. Circulation 82, 2217 (1990); R. J. Bosch, A. S. Woolf, L. G. Fine, Exp. Nephrol. 1, 49 (1993). In these cases, exogenous genes have been applied to the target organ or tissue by direct injection or local instillation of materials. In the kidney, however, the glomeruli are small structures (100–200 μm in diameter) scattered throughout the renal cortex ($3\times10^4$–$1\times10^6$ glomeruli/kidney) and, therefore, cannot be targeted by conventional approaches. Direct injection of viral vectors or DNA-liposome complexes into the renal circulation potentially could cause other renal cell types as well as other organs to be exposed to the exogenous DNA.

Woolf et al., Kidney Int. 43 (Suppl. 39): S116–S119 (1993) disclosed two approaches to gene therapy of the kidney. The first approach involved transplantation of embryonic metanephric tissue that had been transduced with a reporter gene carried by a retrovital vector. In contrast to adult tissue, the embryonic metanephros contains mitotically active cells, required for integration and expression of the retrovital vector. Pieces of the transduced embryonic tissue were transplanted under the renal capsule of adult mice or into the renal cortex of neonatal mice. The authors admitted that long-term survival of the metanephric transplants was limited by ischemia and immune rejection. This approach is dependent on a source of compatible embryonic tissue, and requires surgical intervention in the patient's kidney.

The second approach involved direct injection of retrovirus vectors into kidneys of adult mice. A small number of proximal tubular cells were found to express a reporter gene a few days after injection of retrovirus. Such direct administration of virus creates the possibility for non-kidney tissues and organs to be exposed to the vector. Moreover, since retroviruses require dividing cells for integration and long-term expression, Woolf et al. needed to create a proliferative environment in the adult kidney. They accomplished this by treating the recipient mice with folic acid in order to create generalized and sub-acute damage to the kidney. This, in turn, generated a round of repair proliferation that facilitated integration of the retrovirus vectors. Woolf et al. pointed out that this approach "clearly ... would be unacceptable if gene transfer into human kidneys was contemplated, unless the injury phase could be tightly controlled."

SUMMARY OF THE INVENTION

Disclosed herein is a method of introducing an exogenous gene into a kidney of a mammal, comprising the steps of: providing a plurality of cultured mesangial cells that are immunologically compatible with the mammal and that contain a nucleic acid construct comprising the exogenous gene, and administering the construct-containing mesangial cells to the renal artery of the kidney under conditions where the cells become entrapped in glomeruli of the kidney. The nucleic acid construct may further comprise a replication-defective retroviral sequence and be introduced into the cultured mesangial cells by transfection.

The exogenous gene may comprise a coding sequence for a gene product. The gene product may be expressed, secreted and enter the circulatory system, the interstitial space or urinary tract of the mammal, or the gene product may be expressed, secreted and be localized in the kidney of the mammal or on the mesangial cell surface. The exogenous gene may further comprise a Moloney murine leukemia virus long terminal repeat. The mesangial cells may be administered to one or both renal arteries of the mammal.

Another method of introducing cultured mesangial cells into a kidney of a mammal comprises the steps of: providing a plurality of cultured mesangial cells that are immunologically compatible with the mammal and administering the cultured mesangial cells to the renal artery of the kidney under conditions where the cells become entrapped in glomeruli of the kidney, and selectively damaging the in situ mesangial cells of the kidney with a mesangiolytic agent. Selectively damaging the in situ mesangial cells may occur prior to or after the infusing step. The cultured mesangial cells may contain a nucleic acid construct that comprises an exogenous gene. The mesangiolytic agent may comprise an anti-mesangial cell antibody, and may comprise an anti-mesangial cell monoclonal antibody. A suitable mesangiolytic agent comprises the monoclonal antibody 1-22-3.

A method of introducing cultured mesangial cells into a kidney of a mammal is disclosed, comprising the steps of: providing a plurality of cultured mesangial cells that are immunologically compatible with the mammal and administering the cultured mesangial cells to the renal artery of the kidney under conditions where the cells become entrapped in glomeruli of the kidney.

An article of manufacture comprising packaging material and a plurality of cultured mesangial cells contained within the packaging material is disclosed. The cultured mesangial cells are effective for administration to a renal artery of a mammal under conditions where the cells become entrapped in glomeruli of the kidney and are immunologically compatible with the mammal. The packaging material contains a label or package insert indicating that the cultured mesangial cells can be administered to the renal artery under conditions where the cells become entrapped in glomeruli.

The cultured mesangial cells contained within the packaging material may contain a nucleic acid construct comprising an exogenous gene. The construct-containing mesangial cells may comprise the cell line RM4/BG715.

Also disclosed is an article of manufacture comprising packaging material and a mesangiolytic agent contained within the packaging material. The mesangiolytic agent is effective for selectively damaging the in situ mesangial cells of a kidney of a mammal. The packaging material contains a label or package insert that indicates the mesangiolytic agent can be used for introducing cultured mesangial cells into the kidney of the mammal by steps comprising: providing a plurality of cultured mesangial cells that are immunologically compatible with the mammal, administering the cultured mesangial cells to the renal artery of the kidney under conditions where the cells become entrapped in glomeruli of the kidney, and selectively damaging the in situ mesangial cells of the kidney with a mesangiolytic agent. The mesangiolytic agent may be an anti-mesangial cell antibody, such as the anti-mesangial cell monoclonal antibody 1-22-3.

DETAILED DESCRIPTION OF THE INVENTION

This invention describes a method of site-directed gene delivery to glomeruli of one or both kidneys of a mammal.

In this method, renal glomerular mesangial cells are cultured and transfected outside of the body so as to introduce a gene or genes of interest, and such cells are then administered to a kidney via the renal artery. The administered mesangial cells target glomeruli specifically, and a gene product is expressed within glomeruli. The method may further involve subjecting a kidney to an agent that induces mesangiolysis followed by mesangial regeneration. When engineered mesangial cells are infused into a renal artery supplying such a selectively damaged kidney, expression of an exogenous gene is dramatically amplified in glomeruli and the expression is maintained for at least 8 weeks. Additionally, higher numbers of glomeruli are found to have engineered mesangial cells present than would be expected from infusion of mesangial cells without mesangiolysis.

The present invention represents a novel method that may be used to i) transfer an exogenous gene into specific microscopic structures within an organ, and ii) amplify the introduced gene and its product in situ in a site-specific manner. The method has several advantages compared with conventional in vivo gene transfer using viral vectors or liposomes, e.g., high efficiency, high site-specificity of gene delivery and stable expression. This system allows sophisticated cell engineering to be carried out in vitro prior to injection, and enables the transfer of multiple genes in order to express multiple therapeutic gene products or multiple metabolic pathway components from the glomeruli.

The method uses the renal glomerular mesangial cell for site-specific localization. In the rat glomerulus, the diameter of the capillaries ranges from 5 to 25 μm (afferent arteriole: 25 μm). A. Remuzzi, et al., Am. J. Physiol. 263, F562 (1992). The diameter of cultured rat mesangial cells is about 15–25 μm. When such mesangial cells are injected into the renal artery, the cells lodge or are entrapped within glomerular capillaries. Thus, the site of gene introduction is restricted to glomeruli. In this way, glomeruli (100–200 μm in diameter) scattered throughout the renal cortex can be targeted. In humans, the diameter of mesangial cells likewise is greater than the diameter of the glomerular capillaries. See, e.g., Brenner and Rector (eds.) The Kidney, Vol. I, pp. 10–11 (1991). The present methods are site-specific, in contrast to possible alternatives that use direct injection of viral vectors or DNA-liposome complexes into the renal circulation. Alternative methods expose the entire renal vasculature as well as other organs to virus vectors or DNA-liposome complexes.

For purposes of the present invention, biopsies are taken from a kidney, and mesangial cells are isolated from the biopsy material. Exogenous nucleic acid constructs containing a desired gene or genes are transfected into the isolated mesangial cells. These transfections, or introductions of exogenous genes into the cells, are performed using techniques known to the skilled artisan.

The transfected mesangial cells are administered to a recipient kidney via the renal artery. Cells may be administered by any suitable means, such as infusion or injection. Cells preferably are administered by injection. Because the diameters of the mesangial cells are similar to or less than the inner diameters of the afferent arterioles of glomeruli, but larger than the capillaries within a glomerulus, injected cells are entrapped within glomerular capillaries; entrapment is not detected in other parts of the kidney or in other organs. As such, the transfected mesangial cells populate glomeruli in a site-specific fashion.

Renal glomerular mesangial cells of the invention may be syngeneic, allogeneic, or xenogeneic. Preferred cells are syngeneic or allogeneic, in order to minimize the possibility of immune rejection phenomena. In one embodiment, autologous cells are used in the methods of the present invention. That is, mesangial cells can be cultured from biopsy tissue of one kidney, transfected with a specific gene in vitro, and the stable transfectants injected into the contralateral kidney of the same patient. Alternatively, the transfected mesangial cells can even be administered to the same kidney from which the original biopsy tissue was taken. On the other hand, it is known that many immune rejection phenomena may be controlled or otherwise suppressed by means known in the art. Thus, even xenogeneic cells may be made immunologically compatible, if necessary, by controlling or otherwise suppressing any immune rejection that may occur when practicing the methods of the invention.

An exogenous gene may comprise a coding sequence for a gene product, e.g., a polypeptide. A coding sequence for a gene product may be placed under the control of regulatory elements to ensure effective production of the substance. Regulatory elements may include promoters, repressors, enhancers, polyadenylation regions and the like. Regulatory elements are positioned properly with respect to a coding sequence in order to achieve effective production of the gene product. Some regulatory elements may need to be rather precisely positioned with respect to the coding sequence, whereas the exact position is less restrictive for other regulatory elements. For example, promoters must be positioned 5' to a coding sequence in order to obtain proper initiation of transcription. In contrast, enhancer elements may be active when positioned either 5' or 3' of a transcribed sequence. Majors, J. and Varmus, H., Proc. Natl. Acad. Sci. U.S.A. 80:5866 (1983); Chandler, V. et al., Cell 33:489 (1983); Ponta, H., et al., Proc. Natl. Acad. Sci. U.S.A. 82:1020 (1985).

When an exogenous gene comprises a coding sequence for a gene product, the gene product may be expressed and may remain within the cell, i.e., the gene product may be localized within the expressing mesangial cell. Furthermore, a gene product may be targeted to particular cytoplasmic or nuclear compartments of the mesangial cell. Alternatively, a gene product may be directed to the mesangial cell surface, or may be secreted or otherwise directed to other kidney cell types. Mesangial cells entrapped in the capillaries of glomeruli are ideally positioned to allow diffusion of secreted proteins throughout glomeruli via the capillary lumen, endothelial fenestrae, and mesangial pathways. These pathways allow access for secreted therapeutic products to the systemic circulation, the renal interstitium and the urinary tract. Entrapped cells should not compromise renal function since glomerular capillaries are complex networks with numerous inter-connections, comprising about 400 capillary segments with 250 junctures per glomerulus. A Remuzzi, et al., Am. J. Physiol. 263, F562 (1992). A gene product also may be directed to the circulatory system of the recipient mammal. Sequences useful for directing a gene product to particular cellular locations or to a secretory pathway are known in the art.

The methods of the invention may be used to perform somatic cell gene therapy by introducing therapeutic genes specifically into glomeruli of the kidney. Such an approach is useful for prevention or treatment of such diseases as progressive sclerosis of renal glomeruli or proteinuria. Since mesangial cells become lodged in the vasculature, the cells may deliver polypeptides, DNA, RNA or other therapeutic substances to the systemic circulation in addition to local delivery to the kidney.

Using this methodology, expression of an exogenous gene is detected only from glomeruli of the kidney immediately downstream of the injection site. Expression is not detected in the contralateral kidney or in other organs such as the lungs, where one might expect intravenously injected cells to be entrapped if they had escaped from the kidney.

In an alternative embodiment, cultured mesangial cells are administered to the renal artery of a kidney that has been subjected to an agent that induces transient mesangial regeneration. A mesangiolytic agent may be any agent that selectively damages in situ kidney mesangial cells, i.e., those mesangial cells present in a recipient mammal prior to administration of cultured mesangial cells. For example, an anti-mesangial cell antibody may be introduced into a recipient via the venous circulation, damaging or killing at least some of the in situ mesangial cells by antibody-dependent cell-mediated cytotoxicity (ADCC) or by natural killer cell mechanisms. A few days before or after mesangiolytic agent treatment, cultured mesangial cells having a desired exogenous gene construct are introduced into the kidney via the renal artery. Under these conditions, the present inventor has discovered that expression of an exogenous gene is dramatically amplified in situ and that high level expression continues for extended periods of time. This phenomenon may at least partially reflect an increase in the number of cultured mesangial cells present in the glomeruli.

In a third embodiment, cultured mesangial cells without an exogenous DNA construct are injected into a renal artery of a kidney. The mesangial cells may be tissue typed in order to correspond immunologically as closely as possible to the kidney, by methods known in the art. These cells become entrapped in glomeruli of the kidney, repopulate in the mesangium and begin to perform the normal functions of mesangial cells. Such cells therefore can be useful in treating kidney diseases in which mesangial cells are deficient in number or in function.

The present inventors have observed histological evidence of glomerular injury when reporter cells are injected into damaged and regenerating glomeruli. This means that cultured mesangial cells behave quiescently in the normal environment of glomeruli but may exhibit sclerogenic properties within regenerating glomeruli at least in some circumstances. Thus, transfer of mesangial cells into some forms of diseased glomeruli may accelerate the underlying injury. To eliminate this response, the present inventor has discovered that replication-defective (e.g., mitomycin C-treated) but otherwise viable mesangial cells do not induce such glomerular injury. Thus, use of such cells can result in successful delivery of a foreign gene and its product into the nephritic glomerulus without injury due to the mesangial cells per se.

Mesangial cells are thought to be major factors in the pathogenesis of glomerular disease. M. Kashgarian and R. B. Sterzel, Kidney Int. 41, 524 (1992); W. H. Baricos and S. V. Shah, Kidney Int. 40, 161 (1991). Since glomerular damage and proteinuria induced by antibody is acute and reversible, the disclosed method of antibody treatment and mesangial cell injection offers a new chronic and progressive system of glomerular injury for study of i) the in vivo behavior of cultured mesangial cells, ii) phenotypic differences between mesangial cells within the glomerulus, and iii) underlying mechanisms of glomerular damage. H. Kawachi, et al., Clin. Exp. Immunol. 88, 399 (1992); H. Kawachi, et al, Clin. Exp. Immunol. 90, 129 (1992). The disclosed procedures are also useful for identifying specific gene products that can rescue the glomerulus from progressive sclerosis or prevent proteinuria.

The invention also provides a method for non-local (e.g., systemic) delivery of therapeutic products. This is because gene products released by the mesangial cells into the glomerular capillaries thereby gain access to the systemic circulation, the renal interstitium and the urinary tract, as described above.

The invention will be further understood with reference to the following illustrative embodiments, which are purely exemplary, and should not be taken as limiting the true scope of the present invention as described in the claims.

EXAMPLE 1

Site-Specific Delivery of Cultured Mesangial Cells to the Kidney

A replication-defective retroviral vector, BAG, was used to introduce a reporter gene info mesangial cells. J. Price, D. Turner, C. Cepko, Proc. Natl. Acad. Sci. U.S.A. 84, 156 (1987). This vector has an *Escherichia coli* β-galactosidase coding sequence (Lac-Z) under the control of a Moloney murine leukemia virus long terminal repeat and a neomycin phosphotransferase coding sequence (neo) under the control of a Simian Virus 40 early promoter. Beta-galactosidase activity was used as a reporter for the location of administered mesangial cells, and the neo gene product, which confers resistance to G418, was used as a selectable marker.

BAG DNA was introduced by electroporation into a helper free ecotropic packaging line, ΩE. J. P. Morgenstern, H. Land, Nuc. Acids Res. 18, 3587 (1990). A viral stock having about $4.4 \times 10^4$ X-gal cfu/ml was prepared from the conditioned media of stable transfectants as described in C. Cepko, Methods in Neurosciences, (Academic Press, 1989) vol. 1, chap. 21. The viral stock was tested and shown to be free of helper virus.

Mesangial cells were isolated and cultured from glomeruli of a male Sprague-Dawley rat (250 gm) by standard methods described in M. Kitamura, et al., Kidney Int. 40, 653 (1991). Dulbecco's modified Eagle's medium (DMEM) containing 10% fetal calf serum was used as the cell culture medium. After 4 passages in culture, mesangial cells were infected with BAG virus. Stable transfectants were selected in the presence of 500 μg/ml G418.

To identify a cell line expressing β-galactosidase, samples from selected mesangial cell clones were fixed for 15 minutes at room temperature in phosphate buffered saline (PBS) containing 0.5% glutaraldehyde, 2 mM $MgCl_2$, and 1.25 mM EGTA. After washing repeatedly with ice-cold PBS, cell samples were incubated at 37° C. for 2 hours in X-gal solution. X-gal solution contains 1 mg/ml 5-bromo-4-chloro-3-indolyl β-D-galactopyranoside (Sigma), 5 mM $K_3Fe(CN)_6$, 5 mM $K_4Fe(CN)_6 \cdot 3H_2O$, 2 mM $MgCl_2$, 0.01% sodium desoxycholate and 0.02% Nonidet P40 in PBS (pH 7.4). A high β-galactosidase-expressing clone, RM4/BG715, was identified by this procedure and selected for use in the experiments described below. Non-transfected, cultured mesangial cells do not express β-galactosidase activity.

Clone RM4/BG715 was shown to be a mesangial cell clone by its morphological features and its reaction with three mesangial cell-specific immunological markers. RM4/BG715 cells were cultured on chamber slides and fixed with cold methanol. The cells in separate chamber slides were incubated at 4° C. overnight with one of the first antibody preparations indicated below. Cells were then washed with PBS, and incubated with an FITC-conjugated second antibody at 37° C. for 1 hour. Photographs were taken by fluorescence microscopy. Preparations used as the first antibody were: rabbit anti-desmin anti-serum (Sigma; 1:20 dilution), mouse anti-mesangial cell monoclonal antibody 1-22-3 (1:20 dilution) and mouse anti-α smooth muscle actin monoclonal antibody (Sigma; 1:200 dilution). H. Kawachi, et al., Clin. Exp. Immunol. 88, 399 (1992); H. Kawachi, et al, Clin. Exp. Immunol. 90, 129 (1992). Preparations used as the second antibody were FITC-conjugated goat anti-rabbit immunoglobulin (Sigma; 1:32 dilution), and FITC-conjugated goat anti-mouse immunoglobulin (Sigma; 1:50 dilution). Clone RM4/BG715 showed "hill and valley" formation and positive immunofluorescence staining for desmin, α smooth muscle actin and Thy 1-associated antigen, all of which are characteristics typical of cultured mesangial cells. No replication-competent virus was detected in the conditioned medium of this clone and no evidence of transformation was observed in this cell line in a soft agar colony-formation assay, performed according to the methods of Rizzino, Soft Agar Growth Assays for Transforming Growth Factors and Mitogenic Peptides. In Methods in Enzymology, Peptide Growth Factors, Part A (Barnes and Sirbasku, eds.), Academic Press (1987).

Adult male Sprague-Dawley rats (250–450 g) were anesthetized with a hypnorm-diazepam mixture. The left kidney was exposed through a left flank incision. The kidney was separated from the surrounding fatty tissue and the adrenal gland, and positioned in a kidney cup. The renal artery was then exposed and separated from the renal vein. A cotton thread was passed around the proximal site of the renal artery, and the rats were then left for about ten minutes before cell injection. Confluent RM4/BG715 cells ($0.5-2.5 \times 10^6$ cells, 7–17th passages) were trypsinized, washed once, resuspended in 700 μl of DMEM and injected into the left renal artery using a 27-gauge needle (50–100 μl/sec). To avoid bleeding after injection, the renal artery was clamped with a thread for several minutes and then allowed to reperfuse.

Four of the injected rats were sacrificed at 4 hours. The remaining rats were maintained for 1, 2, 4, 8 or 14 weeks, and two animals were sacrificed at each time period. Both kidneys were removed from the animals, and a portion of each kidney was used for glomerular isolation and another portion was used for preparing frozen sections for microscopy. For glomerular isolation, renal cortices were dissected, diced into small pieces, and forced through a 106 μm mesh screen followed passage through by a 180 μm mesh screen. The resulting filtrate was passed through a 64 μm mesh screen, and washed repeatedly with PBS. Glomeruli remaining on the 64 μm mesh screen were used for the X-gal assay described below. The purity of the isolated glomeruli was more than 95% as judged by phase-contrast microscopy.

Renal tissues and isolated glomeruli were fixed at 4° C. overnight in 2% paraformaldehyde, 0.2% glutaraldehyde, 2 mM $MgCl_2$, and 1.25 mM EGTA in 0.1M piperazine-N,N'-bis[2-ethanesulfonic acid] (PIPES) buffer (pH 6.9). Renal tissues were placed in 2 mM $MgCl_2$ and 30% sucrose in PBS and stored at 4° C. Cryostat sectioning of renal tissues was carried out by procedures known in the art. Fixed glomeruli and fixed frozen renal tissue sections were washed repeatedly at 4° C. with PBS containing 2 mM $MgCl_2$, washed once with 2 mM $MgCl_2$, 0.01% sodium desoxycholate and 0.02% Nonidet P40 in PBS, and then incubated at 37° C. for 2 hours in the X-gal solution described above. The percentage of glomeruli having a blue color, indicative of the X-gal product of β-galactosidase activity, was determined.

The incubation time should be no longer than 2 hours because an endogenous β-galactosidase activity appears in glomerular macrophages after a 12 hour incubation and appears in tubular epithelial cells after a 3–4 hour incubation. In a 2 hour incubation, only β-galactosidase activity due to injected mesangial cells was observed.

The percentage of X-gal positive glomeruli at each time period is shown in Table 1. Injected, cultured mesangial cells were distributed throughout the left kidney and accumulated specifically in glomeruli. Four hours after injection, 39.8% of the glomeruli stained positive in the X-gal assay. X-gal positive glomeruli also were detected at 1, 2, 4, 8 and 14 weeks after injection (Table 1). X-gal staining was detected only in the glomeruli and not in other portions of the left kidney. No X-gal staining was detected in the contralateral kidney (Table 1), or in other organs such as the lungs (data not shown). Injection of a β-galactosidase negative clone, RM4-4, did not result in any X-gal positive staining in the glomeruli of injected kidneys (data not shown), indicating that the enzymatic activity observed with RM4/BG715-injected rat glomeruli was derived from the exogenous β-galactosidase gene present in RM4/BG715 cells. These findings show that cultured mesangial cells are entrapped specifically in renal glomeruli when injected into a renal artery. These findings also show that when an exogenous nucleic acid construct is introduced into cultured mesangial cells, a gene product from construct-containing cells is expressed in glomeruli after injection of such cells.

TABLE 1

Percentage of X-gal positive glomeruli in left and right kidneys after RM4/BG715 cell injection

| Animal | Time after Injection | X-gal positive glomeruli (%) | |
|---|---|---|---|
| | | Left Kidney | Right Kidney |
| 1 | 4 hr | 62 | 0 |
| 2 | 4 hr | 42 | 0 |
| 3 | 4 hr | 37 | 0 |
| 4 | 4 hr | 18 | 0 |
| 5 | 1 wk | 82 | 0 |
| 6 | 1 wk | 65 | 0 |
| 7 | 2 wk | 61 | 0 |
| 8 | 2 wk | 10 | 0 |
| 9 | 4 wk | 76 | 0 |
| 10 | 4 wk | 27 | 0 |
| 11 | 4 wk | 13 | 0 |
| 12 | 4 wk | 4 | 0 |
| 13 | 8 wk | 6 | 0 |
| 14 | 8 wk | 0 | 0 |
| 15 | 14 wk | 3 | 0 |
| 16 | 14 wk | 0 | 0 |

EXAMPLE 2

Enhancement of Expression by Selective Damage to In Situ Mesangial Cells

To selectively damage in situ mesangial cells, an anti-mesangial cell monoclonal antibody, 1-22-3, was used. This antibody recognizes a Thy 1-associated molecule on the surface of rat mesangial cells. H. Kawachi, et al., Clin. Exp. Immunol. 88, 399 (1992); H. Kawachi, et al, Clin. Exp. Immunol. 90, 129 (1992). Five hundred µg of a preparation of 1-22-3 was injected into the tail vein of 10 rats. Active mesangial cell replication peaked on days 4–6. H. Kawachi, et al., Clin. Exp. Immunol. 88, 399 (1992); H. Kawachi, et al, Clin. Exp. Immunol. 90, 129 (1992). When 1-22-3 antibody was injected into the tail vein, selective mesangial damage occurred within 24 hours, followed by transient and specific replication of remnant mesangial cells preceding the reconstruction of normal glomeruli.

RM4/BG715 cells were injected into the left renal artery 3 days after the 1-22-3 treatment. Two rats were sacrificed at 4 hours after and at 1, 2, 4, and 8 weeks after RM4/BG715 cell injection. Renal tissues were sectioned and glomeruli were isolated from each rat as described above. The results of X-gal assays of the tissues and glomeruli are shown in Table 2. Four hours after cell injection, 43 and 67% of the glomeruli in the two animals were stained in the X-gal assay (Table 2). The percentage of glomeruli that had detectable β-galactosidase activity remained at 43% or higher among animals sacrificed at 1, 2, 4 and 8 weeks. In addition, the area of each glomerulus that showed positive staining in the X-gal assay increased dramatically between 4 hours and 1 week. To quantitate this difference, each X-gal positive glomerulus was categorized according to the percentage of glomerular area that was stained with X-gal. Four categories were used: 0–5%, 6–25%, 26–50% and 51–100%. The percentages of X-gal positive glomeruli in each of the four categories are shown in Table 2. None of the X-gal positive glomeruli were stained over a majority (51 to 100%) of the glomerular area at 4 hours after injection. At 1, 2, 4 and 8 weeks after injection, at least 16%, and up to 63%, of the X-gal positive glomeruli stained blue over a majority of the glomerular area.

To further quantitate the increased expression in kidneys treated with a mesangiolytic agent, an X-gal score for each animal was calculated using the following formula:

X-gal score=[(0.025a)+(0.150b)+(0.375c)+(0.750d)][% X-gal positive glomeruli];

where: a=percentage of X-gal positive glomeruli in the 0–5% category, b=percentage of X-gal positive glomeruli in the 6–25% category, c=percentage of X-gal positive glomeruli in the 26–50% category and d=percentage of X-gal positive glomeruli in the 51–100% category.

As shown by the X-gal scores in Table 2, rats sacrificed at 1 week had dramatically increased β-galactosidase activity in situ compared to rats sacrificed at 4 hours. The increased β-galactosidase activity was observed at 2, 4 and 8 weeks, as indicated by the X-gal scores. X-gal scores at 1, 2, 4 and 8 weeks were 6-fold to 15-fold higher than the mean X-gal score at 4 hours (Table 2). These results show that high level β-galactosidase expression was maintained throughout the course of the experiment. As expected, X-gal staining was not detected in other portions of the injected kidneys or in the contralateral kidneys. Selectively damaged rat kidneys that were injected with RM4-4 cells instead of RM4/BG715 cells did not have any X-gal positive staining (data not shown).

TABLE 2

Percentage of X-gal positive glomeruli in rat left kidneys after mesangiolytic treatment and RM4/BG715 cell injection

| Animal | Time | X-gal positive glomeruli (%) | Percent of X-gal positive glomeruli having an X-gal positive area of: | | | | X-gal score | Fold increase in X-gal score |
|---|---|---|---|---|---|---|---|---|
| | | | 0–5% | 6–25% | 26–50% | 51–100% | | |
| 17 | 4 hr | 67 | 81 | 16 | 3 | 0 | 372 | — |
| 18 | 4 hr | 43 | 84 | 14 | 2 | 0 | 213 | — |
| 19 | 1 wk | 72 | 15 | 51 | 18 | 16 | 1928 | 6.6 |
| 20 | 1 wk | 66 | 14 | 18 | 18 | 50 | 3122 | 10.7 |
| 21 | 2 wk | 83 | 9 | 12 | 20 | 59 | 4463 | 15.3 |
| 22 | 2 wk | 78 | 10 | 15 | 21 | 54 | 3968 | 13.6 |
| 23 | 4 wk | 47 | 6 | 12 | 19 | 63 | 2647 | 9.0 |
| 24 | 4 wk | 43 | 17 | 15 | 31 | 37 | 1808 | 6.2 |
| 25 | 8 wk | 81 | 6 | 19 | 21 | 54 | 4162 | 14.2 |
| 26 | 8 wk | 58 | 23 | 15 | 22 | 40 | 2382 | 8.1 |

These results show that the proportion of cultured mesangial cells in a kidney is increased by selectively damaging in situ mesangial cells. Further, the amount of a gene product produced by injected mesangial cells is increased by this method.

EXAMPLE 3

Administration of Cultured Mesangial Cells Prior to Selectively Damaging In Situ Mesangial Cells RM4/BG715 mesangial cells were injected into the left renal artery of rats as described above. Three days later, monoclonal antibody 1-22-3 was injected into the tail vein of each rat. Two weeks after cell injection, rats were sacrificed and X-gal assays carried out as described. In this experiment there was a 4.2 fold increase in the X-gal score at two weeks when compared to the X-gal score 4 hours after RM4/BG715 injection.

EXAMPLE 4

Use of Replication-Defective Mesangial Cells for Site-Directed Gene Delivery

To evaluate the effects of cultured mesangial cell proliferation on amplification of the transfected gene as well as on acceleration of glomerular injury, behavior of mitomycin C-treated RM4/BG715 cells was evaluated. In vitro, mitomycin C treatment inhibited the proliferation of RM4/BG715 cells irreversibly but did not affect expression of β-galactosidase during a 4-week period of observation.

RM4/BG715 cells were treated with 0.2 μg/ml of mitomycin C (Sigma) for 20 hours and then administered to the regenerating kidney according to the methods set out in Example 2, above. Control cells constituted RM4/BG715 cells not treated with mitomycin C (untreated cells). After 7 days, expansion of X-gal-positive areas was completely suppressed in those glomeruli receiving mitomycin C-treated cells, in contrast to those glomeruli receiving untreated cells. The X-gal-positive area in each glomerulus was 2.8±0.1% (mean±SE) in the group receiving treated cells (n=4) vs. 27.5±5.2 in the group receiving untreated cells (n=5). The renal X-gal score (see Example 2, above) was 61±21 for the treated cell group and 2014±288 for the untreated cell group.

Histological analysis revealed that accelerated glomerular injury induced by replication-competent cells was limited in the case of mitomycin C-treated cells. With the replication-defective cells, no evidence of progressive glomerulosclerosis was detected even after 4 weeks, when expression of β-galactosidase was still detected in 11±3.5% (mean±SE, n=4) of glomeruli.

The foregoing detailed description is provided for a better understanding of the invention only and no unnecessary limitation should be understood therefrom as some modifications will be apparent to those skilled in the art without deviating from the spirit and scope of the appended claims.

What is claimed is:

1. A method of introducing cultured mesangial cells into at least one of the two kidneys of a mammal, each said kidney having in situ mesangial cells in glomeruli and supplied by a renal artery, comprising the steps of:

(a) providing a plurality of cultured mesangial cells, said cells immunologically compatible with said mammal; and (b) administering said cultured mesangial cells to at least one of said renal arteries under conditions wherein said cultured mesangial cells become entrapped in said glomeruli of said kidney supplied by said at least one renal artery.

2. A method according to claim 1, wherein said administering step comprises administering a plurality of said cultured mesangial cells to both said renal arteries of said mammal, said cultured mesangial cells becoming entrapped in said glomeruli of both said kidneys.

3. A method according to claim 1, wherein said cultured mesangial cells are autologous to said mammal.

4. A method according to claim 1, wherein said cultured mesangial cells are replication-defective cells.

5. A method according to claim 1, further comprising the step of selectively damaging said in situ mesangial cells of said at least one kidney with a mesangiolytic agent comprising an anti-mesangial cell antibody.

6. A method according to claim 5, wherein said selectively damaging step occurs prior to said administering step.

* * * * *

UNITED STATES PATENT AND TRADEMARK OFFICE
CERTIFICATE OF CORRECTION

PATENT NO. : 5,667,777
DATED : September 16, 1997
INVENTOR(S) : Masanori Kitamura It is certified that error appears in the above-identified patent and that said Letters Patent is hereby corrected as shown below:

Column 2, Line 33: delete "retrovital" and insert --retroviral--

Column 3, Line 2: delete "retrovital" and insert --retroviral--

Column 7, Line 14: delete "retrovital" and insert --retroviral--

Column 7, Line 15: delete "info" and insert --into--

Column 7, Line 32: delete "vital" and insert --viral--

Signed and Sealed this

Ninth Day of December, 1997

Attest:

Attesting Officer

BRUCE LEHMAN

Commissioner of Patents and Trademarks